United States Patent
Li et al.

(10) Patent No.: US 10,486,152 B2
(45) Date of Patent: Nov. 26, 2019

(54) NON-CONTACT MICRO DROPLET DISPENSER AND METHOD

(71) Applicant: Siemens Healthcare Diagnostics Inc., Tarrytown, NY (US)

(72) Inventors: Jay J. Li, Franklin, MA (US); Normand P. Desmarais, Cumberland, RI (US); James E. Rasmussen, Plainville, MA (US); Eric Cowden, Millis, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 269 days.

(21) Appl. No.: 14/784,757

(22) PCT Filed: Apr. 9, 2014

(86) PCT No.: PCT/US2014/033415
§ 371 (c)(1),
(2) Date: Oct. 15, 2015

(87) PCT Pub. No.: WO2014/172152
PCT Pub. Date: Oct. 23, 2014

(65) Prior Publication Data
US 2016/0074857 A1 Mar. 17, 2016

Related U.S. Application Data

(60) Provisional application No. 61/813,700, filed on Apr. 19, 2013.

(51) Int. Cl.
*B01L 3/02* (2006.01)
*G01N 35/10* (2006.01)
*B01L 7/00* (2006.01)

(52) U.S. Cl.
CPC .......... *B01L 3/0265* (2013.01); *B01L 3/0241* (2013.01); *B01L 3/0268* (2013.01); *B01L 7/50* (2013.01);
(Continued)

(58) Field of Classification Search
None
See application file for complete search history.

(56) References Cited

U.S. PATENT DOCUMENTS 3,380,584 A * 4/1968 Fulwyler ................ B01F 13/00
209/127.1
4,213,944 A * 7/1980 Azuhata ................. B01D 53/56
423/235

(Continued)

FOREIGN PATENT DOCUMENTS

JP 2000285847 A 10/2000
JP 2001272640 A 10/2001
(Continued)

OTHER PUBLICATIONS

International Search Report and Written Opinion of International Application No. PCT/US2014/033415 dated Aug. 25, 2014.
(Continued)

*Primary Examiner* — Jill A Warden
*Assistant Examiner* — Brittany I Fisher
(74) *Attorney, Agent, or Firm* — Dunlap Codding P.C.

(57) ABSTRACT

A liquid deposition system comprises a liquid delivery assembly including a dispensing probe having a sidewall including a first end having a liquid port and a second end having a tip, and a flow path opening at the tip and fluidly connected with the liquid port. The system includes a gas injection assembly with a manifold having a gas nozzle, a nozzle opening, and a gas port, the gas nozzle configured to eject a substantially laminar gas stream so that the gas
(Continued)

stream travels through a travel path, the tip of the dispensing probe extending into the travel path. The liquid port is fluidly connectable with a liquid source and the gas port is fluidly connectable with a pressurized gas source, so that a liquid micro droplet is formed at the tip. The laminar gas stream separates the micro droplet from the tip and carries it through the travel path.

14 Claims, 8 Drawing Sheets

(52) U.S. Cl.
CPC ... *B01L 2200/16* (2013.01); *B01L 2300/0838* (2013.01); *B01L 2300/1894* (2013.01); *B01L 2400/02* (2013.01); *B01L 2400/021* (2013.01); *B01L 2400/0487* (2013.01); *B01L 2400/06* (2013.01); *B01L 2400/082* (2013.01); *G01N 2035/1034* (2013.01)

(56) References Cited

U.S. PATENT DOCUMENTS

| | | | |
|---|---|---|---|
| 4,977,785 A | 12/1990 | Willoughby et al. | |
| 7,294,309 B1 * | 11/2007 | Goldberg | B01L 3/0268 222/195 |
| 7,372,566 B2 | 5/2008 | Vesey et al. | |
| 7,824,856 B2 | 11/2010 | Monforte | |
| 8,158,359 B2 | 4/2012 | Leamon et al. | |
| 2003/0168586 A1 | 9/2003 | Yamaguchi et al. | |
| 2003/0170903 A1 | 9/2003 | Johnson et al. | |
| 2004/0238427 A1 | 12/2004 | Maruyama et al. | |
| 2005/0147536 A1 | 7/2005 | Iwata | |
| 2007/0259348 A1 | 11/2007 | Phadke et al. | |
| 2008/0233635 A1 * | 9/2008 | Evans | A61D 19/00 435/287.2 |
| 2009/0095825 A1 | 4/2009 | Ahmadi et al. | |
| 2009/0133410 A1 * | 5/2009 | Thorne | A01N 1/02 62/62 |
| 2010/0143948 A1 | 6/2010 | Gabrin et al. | |
| 2010/0216230 A1 * | 8/2010 | Thorne | A01N 1/02 435/307.1 |
| 2010/0248362 A1 | 9/2010 | Durack et al. | |

FOREIGN PATENT DOCUMENTS

| | | |
|---|---|---|
| JP | 2005292478 A | 10/2005 |
| WO | 9931481 A2 | 6/1999 |
| WO | 02101788 A1 | 12/2002 |
| WO | 2004088283 A2 | 10/2004 |

OTHER PUBLICATIONS

European Search Report and Written Opinion of European Application No. 14784764.4 dated Nov. 9, 2016.
European Office Action of European Application No. 14784764.4 dated Mar. 12, 2018.
Fisher Scientific: "Fisher Isotemp Water Baths"; Feb. 18, 2015 (Feb. 18, 2015); XP055456138; Retrieved from the Internet: URL: <http://www.seas.upenn.edu/~belab/equipment/equipment_links/ Fisher_Water_Bath_Manual.pdf>; pp. 1-4.

* cited by examiner

NON-CONTACT MICRO DROPLET DISPENSER AND METHOD

This application is the U.S. National Stage of International Application No. PCT/US2014/033415, filed Apr. 9, 2014 and claims the benefit thereof. The International Application claims the benefit of U.S. Provisional Application No. 61/813,700, filed Apr. 19, 2013. All of the applications are incorporated by reference herein in their entirety.

BACKGROUND

1. Field of Inventive Concepts

The inventive concepts disclosed herein generally relate to non-contact dispensing of liquids, and more particularly, but not by way of limitation, to non-contact micro droplet dispensers and to methods of using thereof.

2. Brief Description of Prior Art

Advances in diagnostics, particularly in point of care testing, have demonstrated great potential in the commercialization and use of miniaturized test instruments and single-use disposable testing devices which include one or more reagents. In some miniaturized test instruments and single-use disposable testing devices, assay reagents are integrated in microfluidic channels in dry reagent microsphere form that provides significant improvements in reagent stability and shelf life at ambient temperatures.

To that end, devices and methods used in the manufacture of lyophilized reagent microspheres are becoming more important as the demand for lyophilized reagent microspheres increases. One approach to manufacture lyophilized reagent microspheres is to dispense micro droplets of liquid reagent ranging in volume from sub-microliter to a few microliters into liquid nitrogen-containing vessels, or onto liquid nitrogen-cooled solid surfaces, to instantly freeze the reagent droplets into reagent microspheres. The frozen reagent microspheres are then lyophilized, or freeze-dried and/or additionally processed before they are sold and/or used with miniaturized testing devices, for example by being packed in microfluidic channels or chambers.

Examples of currently existing devices used to deposit droplets of liquid onto surfaces generally include two broad categories, i.e., contact and non-contact. In the case of contact devices and methods, physical contact between a dispensing probe carrying a droplet of liquid and a target vessel or surface is used to transfer droplets of liquid from the dispensing probe and onto the target surface or into a vessel. Examples of such contact devices include movable elongated pins which are dipped in a liquid and a droplet of the liquid is transferred to the contact surface via capillary action and/or under the force of gravity.

In the case of non-contact dispensing devices and methods, no physical contact between the dispensing device and the target surface is used, instead, positive droplet displacement is utilized such as via syringe-based liquid dispensers, piezoelectric inkjet-type dispensers, or solenoid-based liquid dispensers, which are positioned at a distance above a target surface and used to deposit reagent droplets thereon. Examples of non-contact dispensing devices include piezoelectric inkjet-type devices and syringe-based devices using gaseous bubbles to separate droplets of reagent.

However, several problems exist in the art when attempts are made to use existing contact and non-contact dispensers to dispense reagent droplets into cryogenically cooled vessels or onto cryogenically cooled surfaces. For example, because liquid nitrogen almost instantly freezes reagent that comes into contact with the liquid nitrogen, contact devices and methods of dispensing droplets into liquid nitrogen or onto liquid nitrogen cooled surfaces are impractical, as the reagent tends to freeze inside the dispensing device and cause malfunctions. Further, with piezoelectric inkjet-type non-contact devices, the inkjet nozzle is typically positioned relatively close to the target surface to dispense the reagent droplets reliably, which results in the reagent and/or the inkjet nozzle becoming frozen by the liquid nitrogen, thus rendering such devices impractical and unreliable for use with liquid nitrogen cooled vessels and/or surfaces.

Multiple unsatisfactory attempts have been made to solve these problems. For example, U.S. publication No. 2007/0259348 describes a method for making a lyophilized reagent pellet on a cryogenically cooled, hydrophobic plate, comprising: introducing a liquid into a dispensing tip; positioning the tip in close proximity to the surface, dispensing a droplet from the tip on the surface (contact dispensing); removing the tip away from the surface so the droplet remains in contact with the surface; maintaining the droplet in contact with the surface for such time as the droplet freezes to form a frozen droplet. This method is a contact dispensing method, and it does not address the problem of the dispensing probe or nozzle becoming frozen as the result of the proximity of the liquid nitrogen.

As another example, U.S. publication No. 2003/0170903 describes a non-contact dispensing apparatus which alternately aspirates a liquid reagent and a gaseous fluid into a passageway, forming air gaps between reagent adjacent droplets. When dispensing, it applies a rapid pressure pulse with a predetermined width to the loaded passageway and dispenses liquid without substantial fluid compression of the air gaps. However, the inventors of the instant inventive concepts have tested this method and have found it doesn't work optimally when used with liquid nitrogen and with certain reagents. The air gap may not always separate the liquid droplets from the dispensing orifice; rather, in some cases the gas from the air gap is blown into the liquid reagent droplet and forms bubbles that are frozen with the droplet, which results in sub-optimal formation of the frozen reagent droplets, differing amounts of reagent between frozen droplets, and variations in shape and size of the frozen droplets.

Further, because various reagents have different compositions of proteins, enzymes, and antibodies and vary in viscosity and surface tension, reagent droplets tend to stick to the tip of the dispensing probe or nozzle with varying amounts of adhesive forces. A challenge not adequately addressed by the prior art is to design a dispenser that is configured to handle different reagents, precisely separate micro droplets from the tip of the probe, and reliably inject the micro droplets into a liquid nitrogen vessel or onto a liquid nitrogen-cooled surface.

Accordingly, a need exists in the art for a non-contact reagent micro droplet dispensers and methods configured to dispense micro droplets in cryogenically cooled vessels or onto cryogenically cooled surfaces. It is to such non-contact reagent micro droplet dispensers and to methods of using thereof that exemplary embodiments of the inventive concepts disclosed herein are directed.

SUMMARY

In one aspect, the inventive concepts disclosed herein are directed to a liquid deposition system comprising a liquid delivery assembly including a dispensing probe having a sidewall including a first end having a liquid port and a second end having a tip, and a flow path opening at the tip and fluidly connected with the liquid port. The system also has a gas injection assembly including a manifold having a gas nozzle, a nozzle opening, and a gas port, the gas nozzle configured to eject a substantially laminar gas stream through the nozzle opening so that the substantially laminar gas stream travels through a travel path, the manifold positioned so that the tip of the dispensing probe extends at least partially into the travel path. The liquid port is fluidly connectable with a liquid source and the gas port is fluidly connectable with a pressurized gas source, so that at least one micro droplet is formed at the tip when a volume of liquid flows through the flow path, and so that the laminar gas stream separates the at least one micro droplet from the tip and carries the at least one micro droplet through the travel path.

In some exemplary embodiments the dispensing probe may extend at least partially through the gas nozzle and through the nozzle opening. The gas nozzle may be substantially cylindrical, and the dispensing probe may extend through the gas nozzle substantially coaxially with the gas nozzle. The tip may be positioned in the travel path such that the substantially laminar gas stream travels substantially parallel to the sidewall. A cryogenically cooled target vessel may have a target opening which may be positioned at a distance below the tip so as to intersect the travel path. The travel path may extend at least partially into the target opening. In some exemplary embodiments the at least one micro droplet separated from the tip may be injected into the target opening by the laminar gas stream, while in some exemplary embodiments a support may movably support the manifold such that the distance between the tip and the target opening is adjustable.

In a further aspect, the inventive concepts disclosed herein are directed to a non-contact micro-droplet dispenser, comprising a support and a valve. The dispenser may further comprise a gas injection assembly supported by the support, including a gas manifold having a gas nozzle and a nozzle opening configured to eject a gas stream so that the gas stream travels through a travel path and a pressurized gas supply line fluidly connected with the gas nozzle and controlled by the valve. The dispenser may also include a liquid delivery assembly including a liquid manifold supported by the support, a dispensing probe having a tip positioned in the travel path, a controller operably coupled with the valve, and a liquid pump operably coupled with the controller and fluidly connected with the dispensing probe, the liquid pump configured to deliver a volume of liquid thereto so that at least one micro droplet is formed at the tip. The gas stream may exert downward force on the micro droplet associated with the tip so that the micro droplet separates from the tip and is carried through the travel path by the gas stream.

In some exemplary embodiments, the dispensing probe may extend through the gas nozzle so that the tip extends a distance past the nozzle opening such that the tip is positioned in the travel path. Further, a target vessel may be positioned at a distance below the tip and may have a target opening positioned so as to intersect the travel path, so that the micro droplet is injected into the target opening by the substantially laminar gas stream. In some exemplary embodiments, a temperature control system may regulate a temperature within the target vessel to a predetermined temperature, for example to at least one of above or below room temperature. In some exemplary embodiments, the target vessel may be selected from a group consisting of a test tube, a vial, a cartridge, a well of a micro titer plate, and a microfluidic device, and/or the distance between the tip and the target vessel may be adjustable. In some exemplary embodiments, a target surface may be positioned at a distance below the tip and may intersect the travel path, and the micro droplet may be placed onto the target surface by the substantially laminar gas stream. A temperature control system may regulate the temperature of the target surface to a predetermined temperature, such as at least one of above or below room temperature, for example. The target surface may be a part of a device selected from a group consisting of a semiconductor wafer, an electronic device, a chip, a glass slide, a plastic substrate, a sensor, a biosensor, and a microarray, for example. The distance between the tip and the target surface may be adjustable.

In yet another aspect, the inventive concepts disclosed herein may be directed to a method of dispensing liquid reagent micro droplets, comprising: (a) forming at least one liquid reagent micro droplet at a tip of a dispensing probe; and (b) contacting the reagent micro droplet with a gas stream external to the dispensing probe to separate the reagent micro droplet from the tip.

In a further aspect, the inventive concepts disclosed herein are directed to a non-contact micro-droplet dispenser, comprising: (1) a plurality of liquid deposition systems, at least two of the liquid deposition systems comprising: (a) a liquid pump assembly; (b) a valve assembly; (c) a liquid delivery assembly including one or more dispensing probes having a sidewall including a first end having a liquid port and a second end having a tip, and a flow path opening at the tip and fluidly connected with the liquid pump: (d) a gas injection assembly including one or more manifolds having a gas nozzle, a nozzle opening, and a gas port connected to the valve, the gas nozzle configured to eject a substantially laminar gas stream through the nozzle opening so that the substantially laminar gas stream travels through a travel path, the one or more manifold positioned so that the tip of the one or more dispensing probe extends at least partially into the travel path; and (e) a controller controlling the liquid pump assemblies and the valve assemblies of the at least two liquid deposition systems to enable the liquid pump to cause at least one micro droplet to be formed at the tip when a volume of liquid flows through the flow path, and control the valve to enable the laminar gas stream to separate the at least one micro droplet from the tip and carries the at least one micro droplet through the travel path. The controller may be configured to independently control the liquid pump and the valve of one of the at least two liquid deposition systems relative to the liquid pump and the valve of another one of the at least two liquid deposition systems.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings:

FIG. 1 is a perspective view of an exemplary embodiment of a non-contact reagent micro droplet dispenser according to the inventive concepts disclosed herein.

FIG. 2 is a side view of the non-contact reagent micro droplet dispenser of FIG. 1.

FIG. 3 is a cross-sectional view taken along line 3-3 of FIG. 2.

FIG. 4 is a magnified partial cross-sectional view along line 4 of FIG. 3.

DETAILED DESCRIPTION

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Finally, as used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

Exemplary embodiments of the inventive concepts disclosed herein are generally directed to a method and apparatus for non-contact, high precision, and microliter-scale dispensing of liquid (e.g., reagent) micro droplets onto a target, such as a surface, or into a container or vial. For example, the container may be a cryogenically cooled vessel (e.g., liquid nitrogen containing vessels) and the surface may be a cryogenically cooled hard or soft surface (e.g., liquid nitrogen cooled). The inventive concepts disclosed herein can be used in semiconductor device fabrication and in this instance, the surface can be a part of a wafer. The inventive concepts disclosed herein can also be incorporated into a diagnostic instrument for providing non-contact dispensing of droplets onto a sensor, a biosensor or a microarray. The surface can be a part of a semiconductor wafer, electronic device, a chip, a glass substrate, such as a glass slide, or a plastic substrate. The container may be a test tube, vial, cartridge, well of a micro-titer plate, or a microfluidic device.

In an exemplary embodiment, a micro droplet dispenser and a dispensing method according to the inventive concepts disclosed herein may utilize a gas nozzle to provide a pulsed and laminar gas stream travelling through a travel path, and a dispensing probe having a tip positioned in the travel path so that the laminar gas stream applies downward force to a liquid reagent micro droplet adhering to the tip of the dispensing probe, to separate the micro droplet from the tip and to inject the separated micro droplet into a cryogenically cooled target vessel. As used herein, the laminar gas stream includes a gas or mixture of gases that travels through a travel path which is substantially linear. The inventive concepts disclosed herein may be provided with suitable hardware/software to regulate the temperature of the surface or within the target vessel so as to maintain the temperature of the surface or within the target vessel above room temperature, at room temperature, or below room temperature. For example, a temperature control system can be used. The temperature control system may have one or more heat exchanger associated with the surface or with the target vessel, one or more temperature sensors to determine the temperature of the surface or within the target vessel, as well as a controller to regulate the one or more heat exchanger based upon input from the one or more temperature sensors, for example.

In some embodiments, the dispensing probe may extend through the gas nozzle so that the tip of the dispensing probe is positioned outside of the gas nozzle and in the travel path. For example, the tip of the dispensing probe may be positioned at least 1-2 millimeters beyond the gas nozzle, yet within a portion of the laminar gas stream applying sufficient force to the micro droplets to separate the micro droplets from the tip. Further, when the dispensing probe is being utilized to dispense the micro droplets into the cryogenically cooled vessel or onto the cryogenically cooled surface, the tip should be spaced a distance above a target opening of the cryogenically cooled vessel, to prevent the liquid (e.g., reagent) inside the dispensing probe from freezing, for example. In some exemplary embodiments, the dispensing probe and the gas nozzle may be movably supported above the cryogenically cooled target vessel (e.g., movable relative to one another and/or relative to the target vessel), so that the position of the tip of the probe in the travel path may be adjusted relative to a nozzle opening to optimize the separation of the micro droplets from the tip, and so that the distance between the tip and the target opening of the target vessel may be adjusted to prevent freezing of the liquid reagent at the tip or inside the dispensing probe, for example. The micro droplets may be guided or injected into the target vessel by the laminar gas stream travelling through the travel path. Frozen reagent microspheres produced according to the inventive concepts disclosed herein may be substantially uniform in size and shape and may be lyophilized and/or otherwise processed and incorporated into testing devices as will be appreciated by persons of ordinary skill in the art.

Referring now to the drawings, and to FIGS. 1-5, in particular, an exemplary embodiment of a non-contact micro droplet dispenser 100 according to the inventive concepts disclosed herein may include a liquid deposition system 101, a controller 106, and an optional support 108 supporting the liquid deposition system 101 a distance above a target vessel 110. The non-contact micro droplet dispenser 100 will be described herein for forming lyophilized reagent microspheres. However, it should be understood that the non-contact micro droplet dispenser 100 can be used for many other types of precision non-contact dispensing of droplets of a liquid. For example, the non-contact micro droplet dispenser 100 can be used for non-contact dispensing of micro droplets onto a surface or into a vial. Further, the liquid dispensed by the non-contact micro droplet dispenser 100 may not include reagents. For example, the liquid dispensed by the non-contact micro droplet dispenser 100 can be an aqueous organic solvent based chemical, a polymer liquid, a biological liquid, a pharmaceutical agent liquid, and mixtures thereof.

The liquid deposition system 101 includes a gas injection assembly 102 and a liquid delivery assembly 104.

Figure 5:
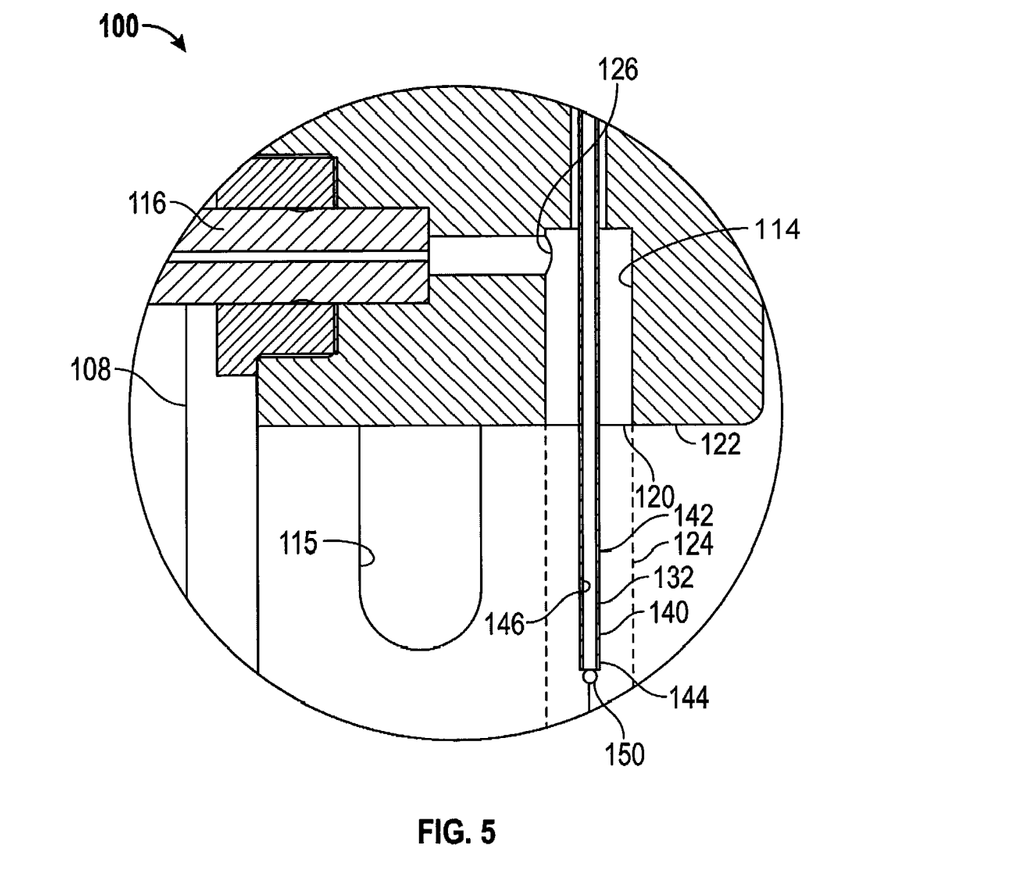
FIG. 5 is a magnified partial cross-sectional view along line 5 of FIG. 4.
Figure 6:
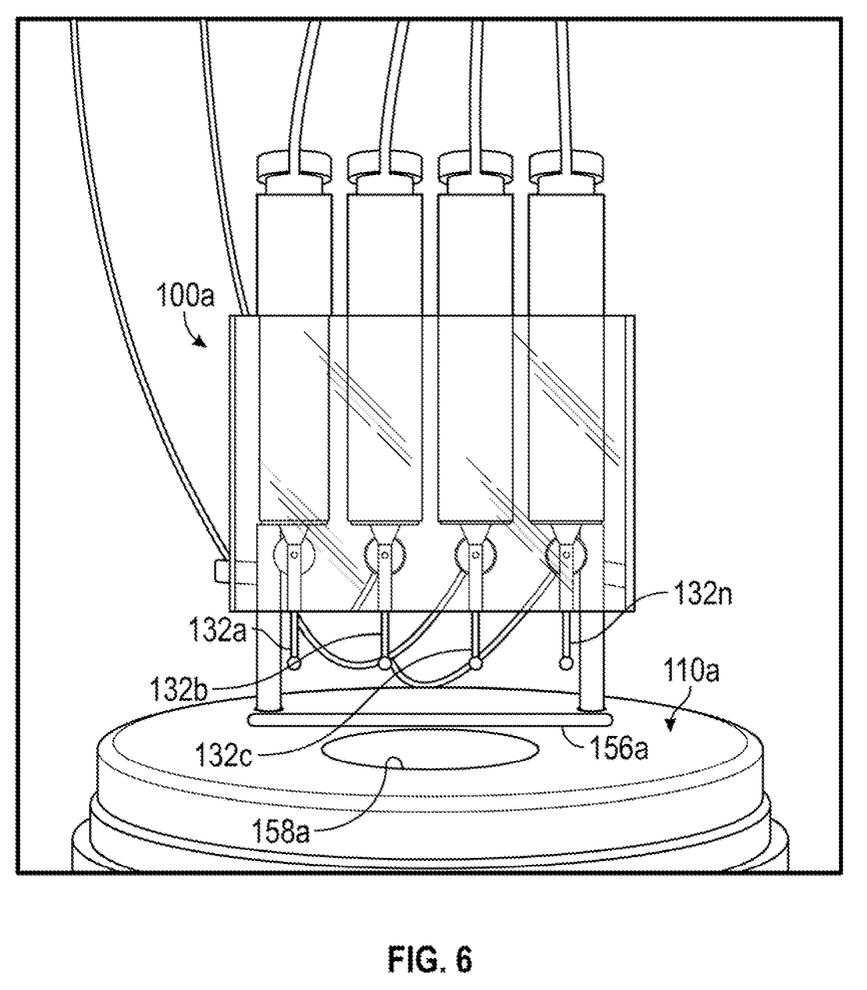
FIG. 6 is a diagram of an exemplary embodiment of a multi-channel non-contact reagent micro droplet dispenser according to the inventive concepts disclosed herein.
Figure 7:
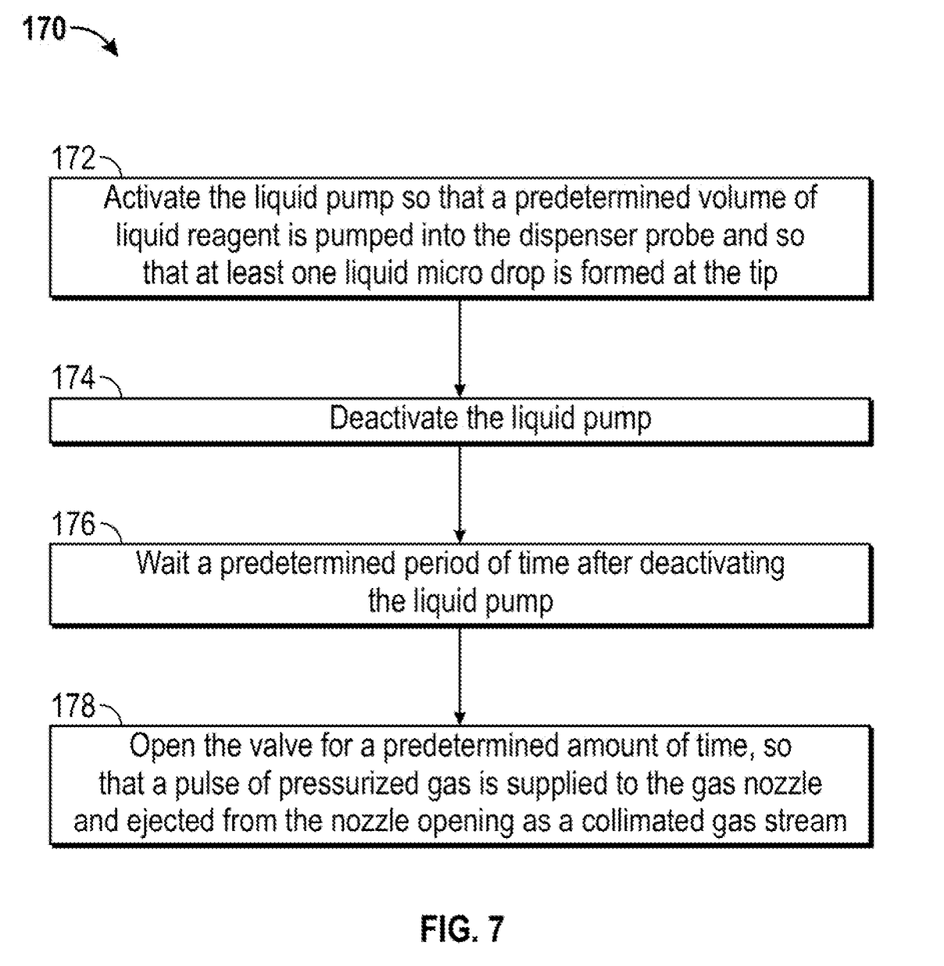
FIG. 7 is a diagram of an exemplary embodiment of a method of non-contact reagent micro droplet dispensing according to the inventive concepts disclosed herein.
Figure 8:
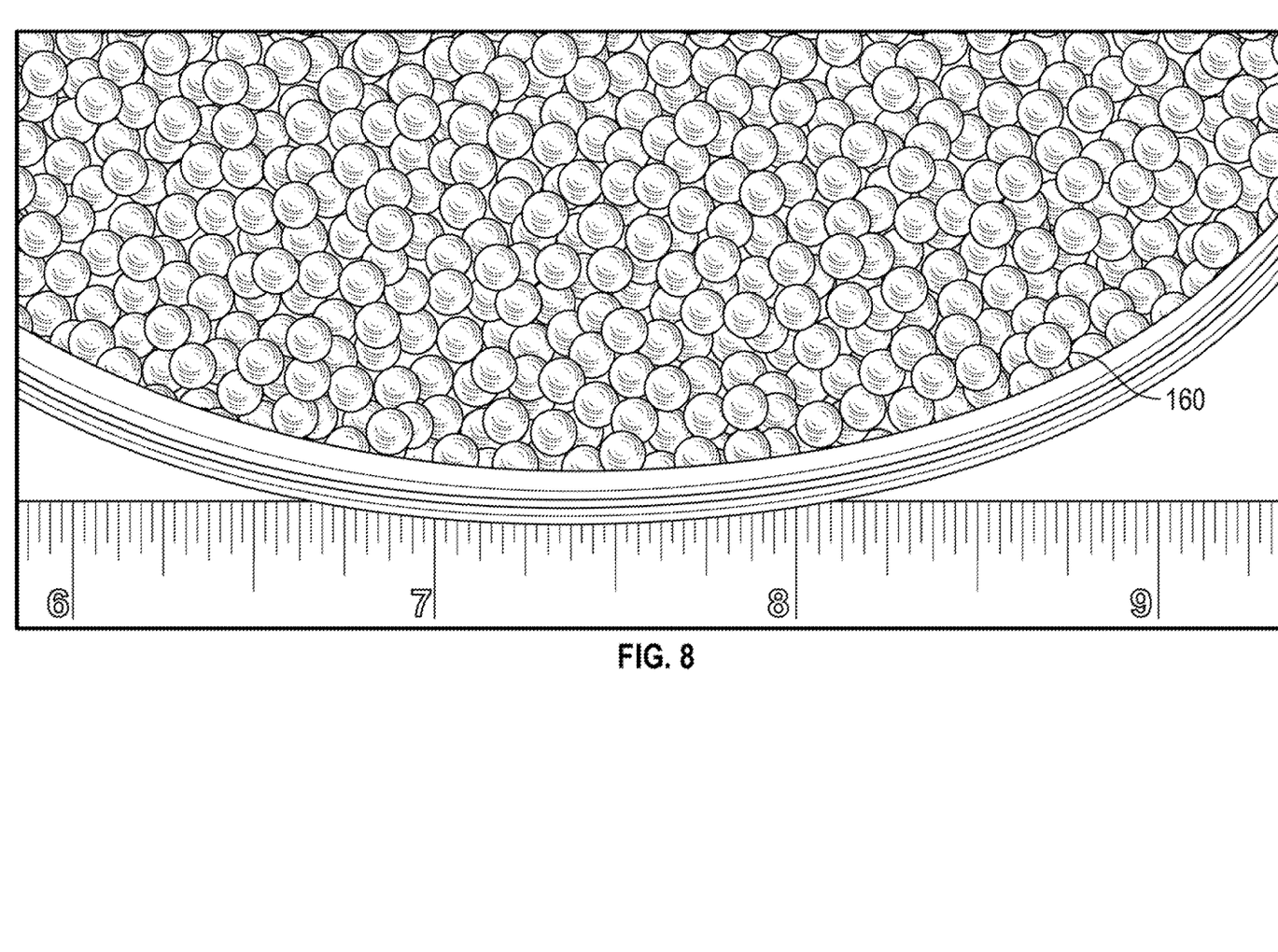
FIG. 8 is a diagram of an exemplary embodiment of frozen reagent microspheres according to the inventive concepts disclosed herein.

The gas injection assembly 102 may include a gas manifold 112 having a gas nozzle 114 (See FIG. 5). A pressurized gas supply line 116 may be fluidly connected with the gas nozzle 114.

The gas manifold 112 may be movably associated with the support 108 in any desired manner so that the support 108 may support the gas manifold 112 at a distance above the target vessel 110, and so that the distance between the gas manifold 112 and the target vessel 110 may be adjusted in the vertical direction as desired. For example, an elongated slot 115 may be formed into the support 108, and a set screw 118 may be inserted through the slot 115 and into a threaded opening (not referenced) formed into the gas manifold 112 so that the gas manifold 112 may be slidably movable relative to the support 108 and the target vessel 110, and so that the gas manifold 112 may be secured at any desired height above the target vessel 110 by tightening the set screw 118. The gas manifold 112 may be associated with any desired support, such as the support 108, so that the position of the gas manifold 112 may be adjusted in the vertical or Z-direction relative to the target vessel 110, such as for example via a telescoping support, a servo, a hydraulic or pneumatic arm, a threaded guide rod, or combinations thereof, for example. It is to be understood that in some exemplary embodiments the position of the gas manifold 112 may be adjustable in all three dimensions, such as by implementing the support 108 as a robotic arm or movable arm configured to move in two-dimensions, or three-dimensions, or more dimensions, for example.

The gas manifold 112 may be constructed of any desired material having sufficient strength and durability to receive a pulse of pressurized gas and direct the pulse of pressurized gas as described below. Exemplary materials include plastics, metals, alloys, non-metals, resins, and combinations thereof.

The gas nozzle 114 may be formed in the gas manifold 112 in any desired manner, and may include a nozzle opening 120 which intersects a bottom surface 122 of the gas manifold 112 (FIG. 5). The gas nozzle 114 may also include an opening (not referenced) configured to slidably receive a dispensing probe of the liquid delivery assembly 104 therein as will be described below, and an optional set screw 119 may be used to secure the dispensing probe at any desired position, for example.

It is to be understood that while the gas nozzle 114 is shown as being substantially cylindrical in shape, the gas nozzle 114 may have any desired shape, size, cross-section, and dimensions, provided that the gas nozzle 114 is configured to collimate a stream of compressed gas and to eject or emit a laminar gas stream out of the nozzle opening 120 so that the laminar gas stream travels through a travel path 124 and desirably disperses minimally along the travel path 124. For example, the travel path 124 may at least partially or substantially completely span the distance between the nozzle opening 120 and the target vessel 110, and/or may intersect a target opening of the target vessel 110 as will be described below.

Figure 1:
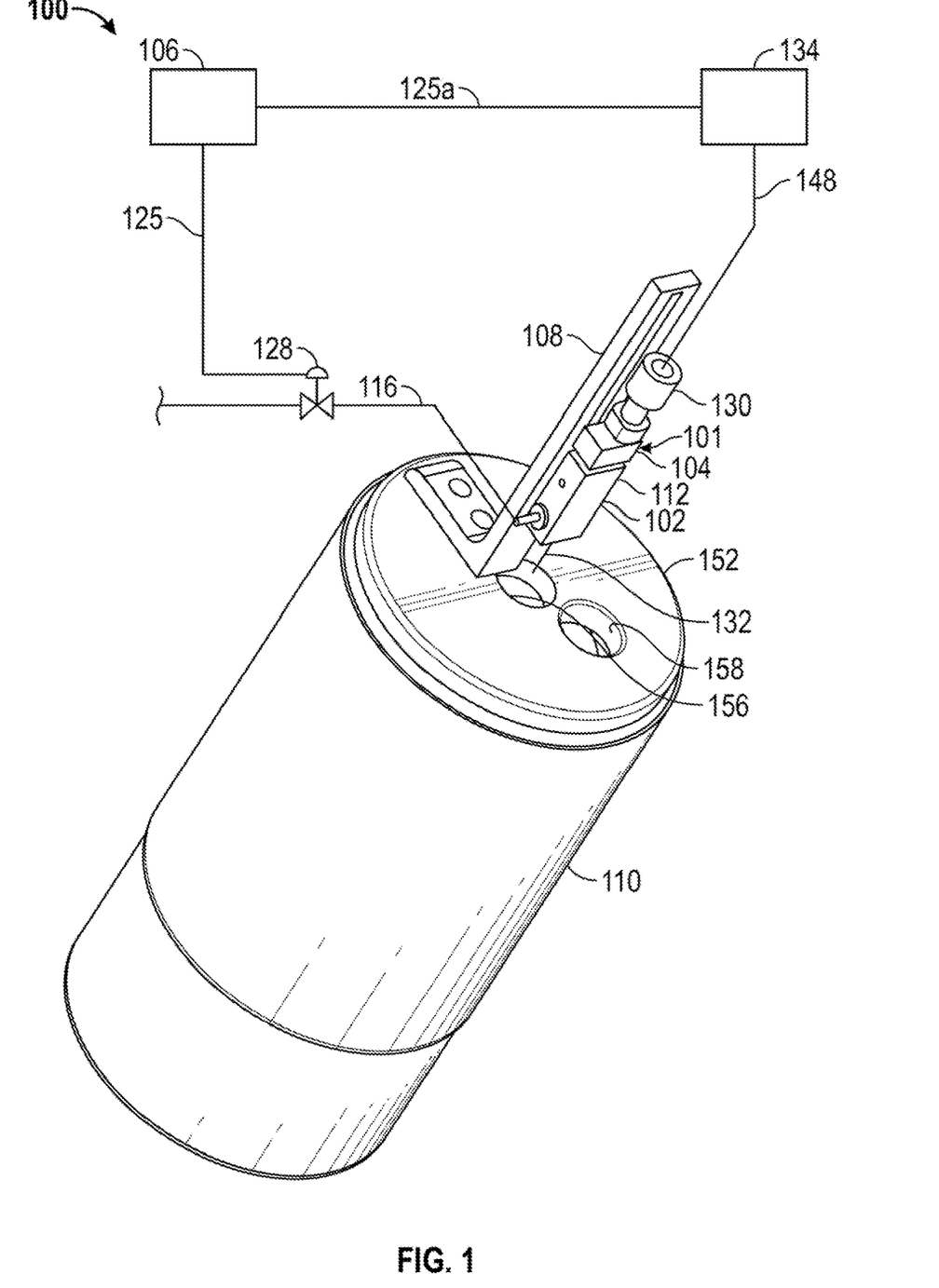

The pressurized gas supply line 116 may be in fluid communication with the gas nozzle 114 via a gas port 126 in fluid communication with the gas nozzle 114 at any point above the nozzle opening 120 so that a volume of compressed gas may be injected or otherwise introduced into the gas nozzle 114. For example, the gas port 126 may be fluidly connected with the pressurized gas supply line 116 and the flow of pressurized gas through the gas port 126 may be controlled by a valve 128 (FIG. 1). For example, the valve 128 may be selectively opened to allow a volume of pressurized gas to be introduced into the gas nozzle 114, and closed to discontinue the supply of pressurized gas into the gas nozzle 114. In some exemplary embodiments, the valve 128 may be operably coupled with the controller 106 via a control line 125 so that the controller 106 may open and/or close the valve 128 as desired (e.g., by providing a control signal to the valve 128 for a predetermined amount of time, or for a predetermined duration or pulse). The valve 128 may be implemented as a solenoid, a ball valve, a gate, or in any other desired manner, for example.

The pressurized gas supply line 116 may be fluidly connectable with any desired source of pressurized gas (not shown), such as a pressurized vessel or tank, or a compressor, for example. The pressurized gas supplied to the gas nozzle 114 via the pressurized gas supply line 116 may be any desired gas (or mixture of gasses) that is substantially inert with respect to the particular liquid or reagent dispensed by the micro droplet dispenser 100, such as nitrogen, argon, atmospheric air, or combinations thereof, for example. Any desired volume of compressed gas may be supplied to the gas nozzle 114 at a pressure sufficient to generate a laminar gas stream to separate and inject one or more liquid micro droplets into the target vessel 110 as will be described below. One or more pressure regulators (not shown) or other devices may be fluidly connected with the pressurized gas supply line 116 upstream or downstream of the valve 128, for example.

Figure 2:
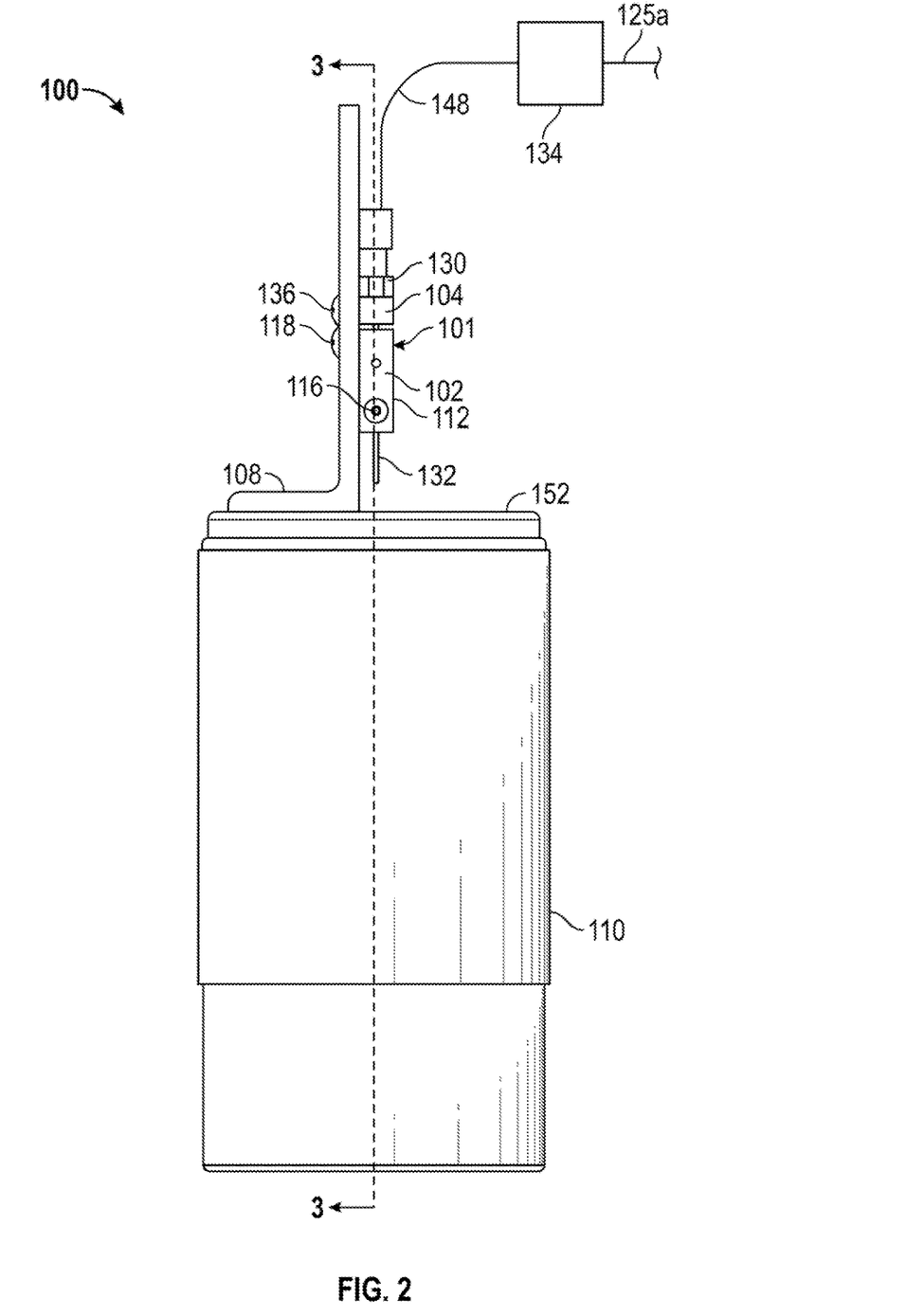
Figure 3:
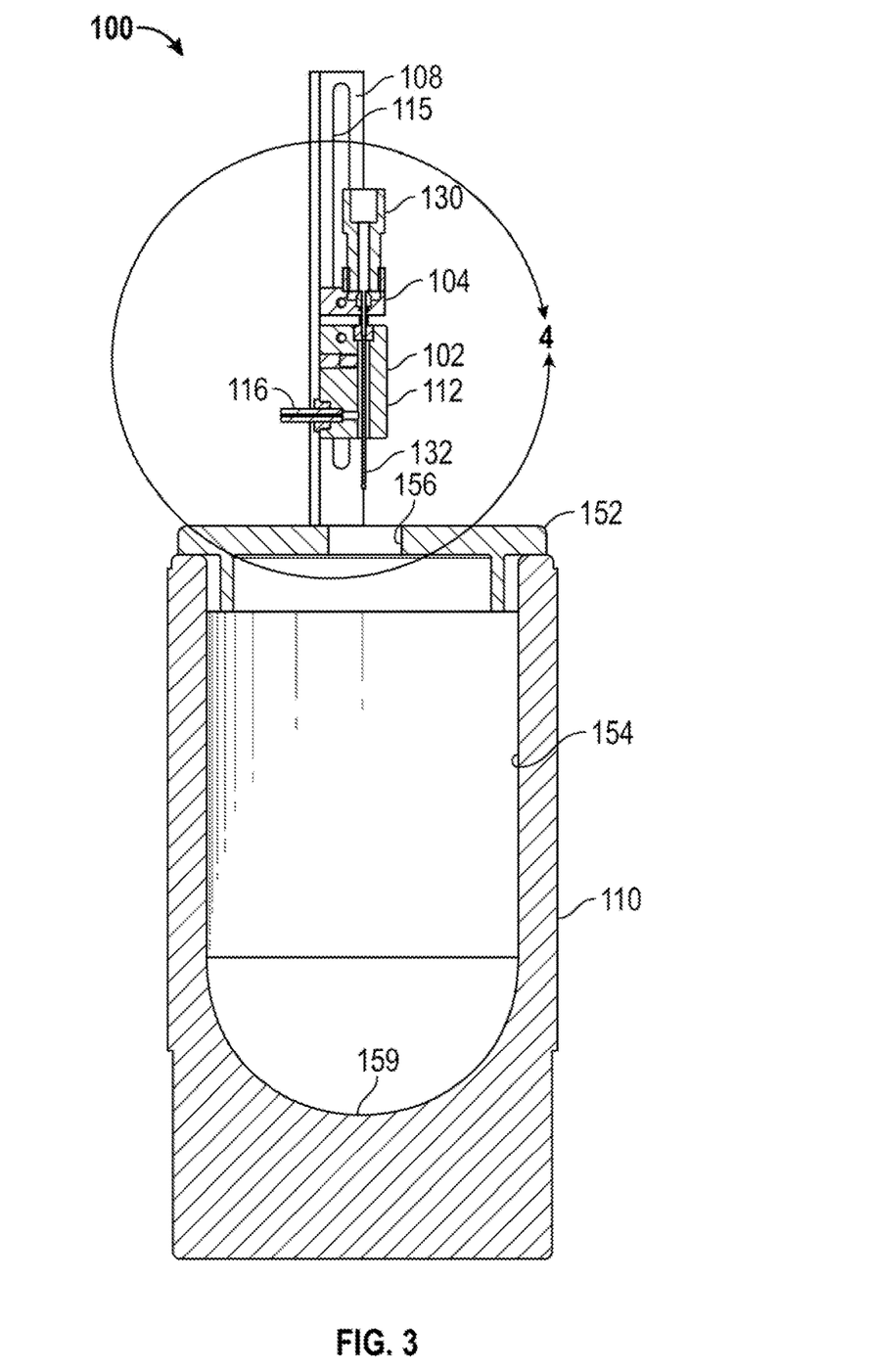

The liquid delivery assembly 104 may include a liquid manifold 130 (FIG. 2) and a dispensing probe 132 (FIG. 2) fluidly connectable with a liquid pump 134 (FIG. 2).

Figure 4:
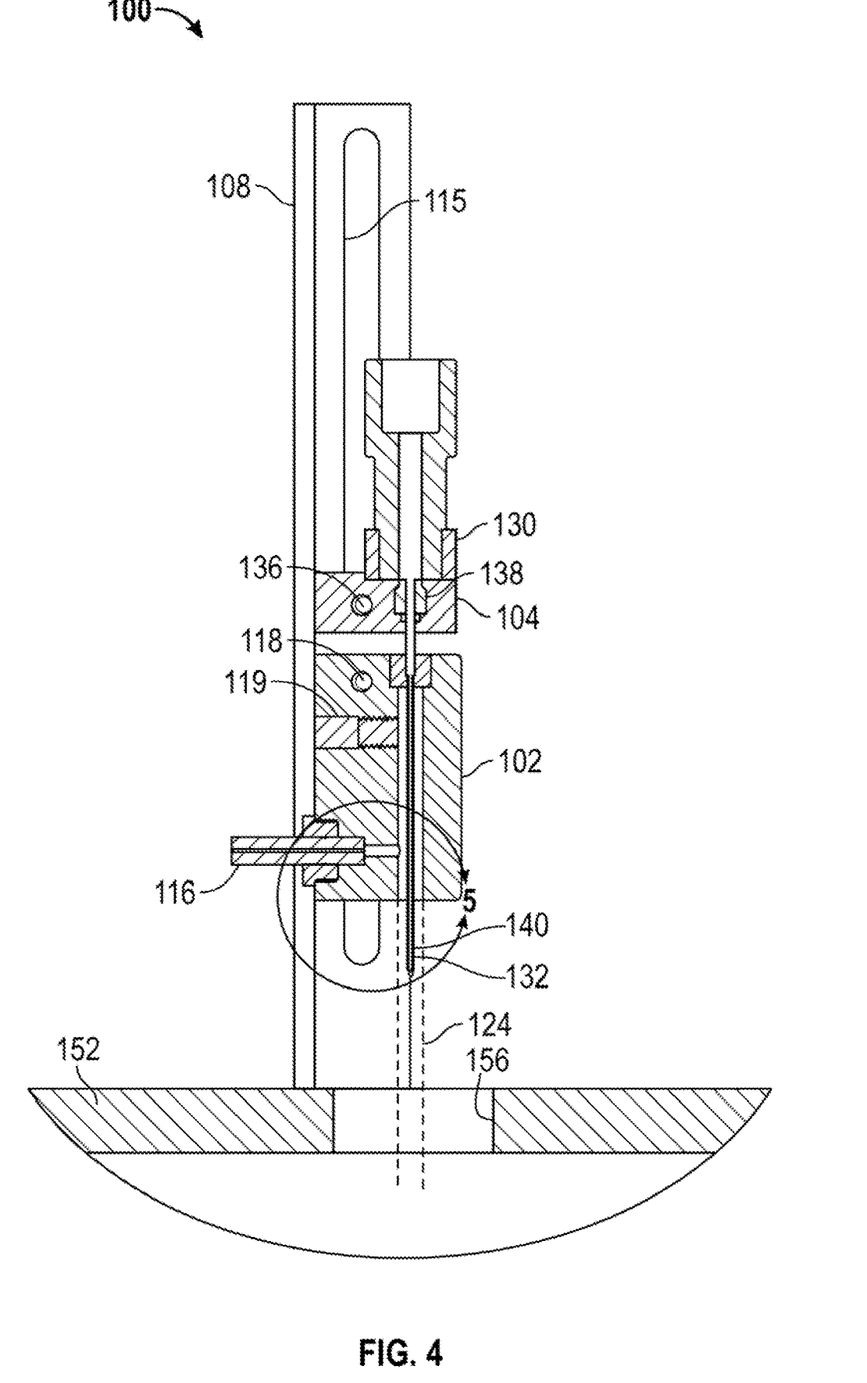

The liquid manifold 130 may be implemented similarly to the gas manifold 112 and may be adjustably supported by the support 108 above the gas manifold 112 so that the dispensing probe 132 extends at least partially through the gas nozzle 114 (e.g., slidably), and at least partially into the travel path 124 as shown in FIG. 4. The liquid manifold 130 may be spaced apart a distance from the gas manifold 112 so that the distance between the liquid manifold 130 and the gas manifold 112 may be adjusted as desired to optimize the injection of micro droplets into the target vessel 110, as will be described in detail below. Further, in some exemplary embodiments the liquid manifold 130 and the gas manifold 112 may be implemented as a unitary component.

The liquid manifold 130 may be movably associated with the support 108 similarly to the gas manifold 112 so that the position of the liquid manifold 130 may be adjusted in the vertical or Z-direction relative to the support 108 and/or to the target vessel 110. For example, the liquid manifold 130 may be movably associated with the support 108 via a set screw 136 inserted through the elongated slot 115 formed in the support 108 and through a threaded opening (not referenced) formed in the liquid manifold 130 so as to allow adjusting the position of the liquid manifold 130 in the vertical direction and securing the liquid manifold 130 at any desired position by tightening the set screw 136. In some exemplary embodiments, the liquid manifold 130 may be adjustable in all three dimensions similarly to the gas manifold 112 as described above, for example.

The dispensing probe 132 may have a first end 138, a second end 140, and a sidewall 142 extending from the first end 138 to the second end 140, and may have a flow path 146 (FIG. 5) extending therethrough, substantially from the first end 138 to the second end 140, for example. The second end 140 may end in a tip 144, and the flow path 146 may open at the tip 144 of the second end 140, for example.

The dispensing probe 132 may be implemented as a stainless steel needle (e.g., having a gauge varying between 18 and 29), a stainless steel tube, a polytetrafluoroethylene needle or tube, or as a polytetrafluoroethylene-lined stainless steel tube, or may be constructed of any other suitable material substantially inert with respect to the reagents used with the micro droplet dispenser 100, for example. In some exemplary embodiments, the dispensing probe 132, the flow path 146, the sidewall 142, and/or the tip 144 may be lined or coated with one or more materials or substances so as to change the surface tension and/or other properties of the dispensing probe 132.

The first end 138 may be associated with the liquid manifold 130 in any desired manner and may be in fluid communication with the flow path 146. The first end may be fluidly connectable with the liquid pump 134 via a reagent intake line 148 (FIG. 2) so that a volume of liquid is pumped through the flow path 146 by the liquid pump 134 as will be described below. An optional fitting or liquid port (not referenced) may be used to fluidly connect the reagent intake line 148 to the first end 138 in some embodiments.

The sidewall 142 may have any desired outer diameter, such as an outer diameter varying between about 0.050 inches (or 1.27 mm) and about 0.1325 inches (or 0.3366 mm), for example. Further, the sidewall 142 may have any desired thickness, such as a thickness varying between about 0.0085 inches (or 0.216 mm) and about 0.003 inches (or 0.0762 mm), for example. The flow path 146 may have a substantially cylindrical or any other desired cross section and may have any desired internal diameter, such as an internal diameter varying between about 0.136 inches (or 3.429 mm) and about 0.00725 inches (or 0.184 mm), for example.

The flow path 146 defined by the dispensing probe 132 may open at the tip 144, such that at least one micro droplet 150 may form at the tip 144 when a liquid, such as a liquid reagent, flows through the flow path 146. The at least one micro droplet 150 may be associated with the tip 144 in any desired manner, such as surface tension of the liquid (e.g., a reagent), adhesion-type forces between the at least one micro droplet 150 and the flow path 146, the tip 144, and/or the sidewall 142, for example. The micro droplet 150 may have a substantially spherical shape, for example, and may have any desired volume, such as a volume varying between about 0.3 microliters and about 3 microliters. As will be appreciated by persons of ordinary skill in the art, the smaller the thickness of the sidewall 142 is, the higher the precision of the micro droplet dispenser 100 may be (e.g., the more accurately the volume of the micro droplet 150 may be adjusted).

Further, while the tip 144 is shown as a substantially flat tip 144 (extending normal with respect to the sidewall 142), in some exemplary embodiments of the inventive concepts disclosed herein, the tip 144 may extend at a non-normal angle with respect to the sidewall 142, or may have a first portion having a first angle and a second portion having a second angle intersecting with first portion. The shape and/or angle of the tip 144 with respect to the sidewall 142 may be varied with various liquids and/or reagents as will be appreciated by persons of ordinary skill in the art having the benefit of the instant disclosure.

As will be appreciated by persons of ordinary skill in the art, the shape and angle of the tip 144, the thickness and the outer diameter of the sidewall 142, the internal diameter of the flow path 146, and the material from which the dispensing probe 132 is constructed, along with the chemical composition, density, and surface tension of the liquid reagent used, and gravity may have a separate and/or combined effect on the volume and shape of the micro droplet 150 by determining the amount of adhesive and/or surface tension forces associating the micro droplet 150 and the tip 144. In some exemplary embodiments, optimal results in terms or reliability and consistency of the volume and shape of the micro droplets 150 may be achieved by minimizing the contact area between the micro droplet 150 and the tip 144, which may be achieved by manipulating one or more of the above factors. For example, one or more of the thickness of the sidewall 142, the shape of the tip 144, the internal diameter of the flow path 146, the surface tension of the flow path 146 and/or the reagent used, may be varied.

The dispensing probe 132 may extend at least partially or substantially completely through the gas nozzle 114 so that the second end 140 extends past the nozzle opening 120 and so that the tip 144 is positioned at least partially in the travel path 124 such that the laminar gas stream travelling through the travel path 124 exerts downward force on the micro droplet 150 (FIG. 5) associated with or adhering to the tip 144 to separate the micro droplet 150 from the tip 144. The tip 144 may be positioned at a distance above the target vessel 110, such as at a distance varying between about 1 cm and about 3 cm (including any ranges and sub-ranges therebetween) or a distance of about 2 cm, for example. As will be appreciated by persons of ordinary skill in the art, any distance between the tip 144 and the target vessel 110 may be implemented so that the liquid reagent inside the dispensing probe 132 and/or the micro droplet 150 associated with the tip 144 do not freeze, and so that the micro droplet 150 stabilizes into a substantially spherical shape as it travels through the travel path 124 between the tip 144 and the target vessel 110, for example.

In the exemplary embodiment shown in FIGS. 1-5, the dispensing probe 132 is shown as extending substantially coaxially with, and substantially parallel to, the gas nozzle 114 so that the travel path 124 is substantially parallel to the sidewall 142 of the dispensing probe 132 and so that the laminar gas stream moves substantially parallel to the dispensing probe 132 and to the tip 144. It is to be understood that in some exemplary embodiments, the dispensing probe 132 may not be coaxial with the gas nozzle 114 and/or may be angled relative to the gas nozzle 114 at any desired angle, provided that the tip 144 at least partially extends below the nozzle opening 120 and/or is at least partially positioned in the travel path 124 of the laminar gas stream.

The liquid pump 134 may be implemented as a high-precision microliter scale pump, such as a syringe pump or a high-precision peristaltic pump, for example, and is configured to deliver a desired liquid volume to the flow path 146 of the dispensing probe 132. The liquid pump 134 may be fluidly connectable with the first end 138 of the dispensing probe 132 via the reagent intake line 148, and may be configured to be operably coupled with the controller 106 via a control line 125*a*, so that the controller 106 may supply one or more control and/or power signals to the liquid pump 134. In some exemplary embodiments, the controller 106 may provide a control signal or pulse having a predetermined duration to the liquid pump 134 to turn the liquid pump 134 on and off as desired. Further, in some exemplary embodiments, the controller 106 may operate the liquid pump 134 at a first speed or output volume for a first period of time, and then operate the liquid pump 134 at a second speed or output volume for a second period of time, with the first speed or output being significantly larger than the second speed or output volume. In these exemplary embodiments, the controller 106 is preferably configured to synchronize the dispensing of the liquid via the liquid pump 134 with the operation of the valve 128 such that the valve 128 is opened while the liquid pump 134 is operated at the second speed.

The liquid pump 134 may also be fluidly connected with any desired liquid source such as a liquid reservoir or tank (not shown) so that the liquid pump 134 may withdraw a volume of any desired liquid reagent or other liquid from the liquid source, and dispense the volume of liquid via the dispensing probe 132 by forming the at least one micro droplet 150 on the tip 144.

The controller 106 may be configured to be operatively coupled with a liquid pump, such as the liquid pump 134 via the control line 125*a*. Further, the controller 106 may be configured to be operatively coupled with the valve 128 via the control line 125 so that the controller 106 may control the operation of the micro droplet dispenser 100 by controlling the operation of the valve 128 and the liquid pump 134, for example. The controller 106 may be implemented as any desired analog or digital device, and may include one or more processor working together or independently to execute processor executable code stored in one or more non-transitory computer medium operably coupled with the at least one processor in some exemplary embodiments. Further in some exemplary embodiments, the controller 106 may be implemented as a hardware device such as a field-programmable gate array, an application specific integrated circuit, a desktop computer, a workstation, a laptop, a portable wireless device, a smartphone, and combinations thereof, and/or may communicate with the liquid pump 134 and/or the valve 128 by exchanging data and/or one or more signals over a computer network.

The target vessel 110 may be implemented as a cryogenically cooled container, such as a vacuum flask or a dewar, for example, and may have a lid 152 and a cryogenic coolant chamber 154. The target vessel 110 may be associated with the support 108, or may be separate from the support 108 provided that the gas injection assembly 102 is positioned above the target vessel 110 so that the travel path 124 extends between the gas injection assembly 102 and the target vessel 110, for example.

As shown in FIG. 1, the lid 152 may include a target opening 156 and an optional vent 158. The target opening 156 may have any desired size and shape, and may be positioned below the tip 144 and separated a distance therefrom such that the target opening 156 intersects the travel path 124 (FIG. 4), for example. The laminar gas stream traveling through the travel path 124 may direct or inject the at least one micro droplet 150 into the cryogenic coolant chamber 154 via the target opening 156, in some exemplary embodiments. In some exemplary embodiments, the travel path 124 may extend at least partially into the target vessel 110 and/or into the target opening 156. Further, in some exemplary embodiments, the travel path 124 may end at the target opening 156, or at a distance above the target vessel 110.

The optional vent 158 may have any desired shape and size and may be configured to vent any evaporated cryogenic coolant from the cryogenic coolant chamber 154 and/or any gas from the laminar gas stream entering the target vessel 110 via the target opening 156, for example. In some exemplary embodiments, the vent 158 may be omitted and the target opening 156 may function as a vent.

The cryogenic coolant chamber 154 may be configured to contain any desired volume of liquid nitrogen or any other desired cryogenic coolant and may have any desired size and cross-section, as will be appreciated by a person of ordinary skill in the art. In some exemplary embodiments, the cryogenic coolant chamber 154 may have a substantially concave bottom 159 to optimize the freezing of micro droplets 150 injected into the cryogenic coolant chamber 154 by the micro droplet dispenser 100.

An optional temperature control system (not shown) may be operably coupled with the target vessel 110 so that the temperature control system may control the temperature within the target vessel 110 and may maintain such temperature above room temperature, at room temperature, or below room temperature, for example. The temperature control system may have one or more temperature sensors (not shown) positioned so as to detect the temperature inside the target vessel 110, at the target opening 156, and/or just above the target opening 156, and combinations thereof, for example.

It is to be understood that in some exemplary embodiments of the inventive concepts disclosed herein, the target vessel 110 may be omitted and a liquid nitrogen cooled solid surface, or other cryogenically cooled solid surface may be implemented instead, onto which surface micro droplets 150 may be dispensed by the micro droplet dispenser 100. Further, the micro droplet dispenser 100 can be used to dispense the micro droplets 150 onto a test device (not shown).

In operation, the micro droplet dispenser 100 may generally operate as follows. Any desired liquid, such as a liquid reagent, may be supplied to the liquid pump 134. The liquid pump 134 may be fluidly connected with the flow path 146 and may be activated by the controller 106 so that the liquid pump 134 pumps a predetermined volume of the liquid reagent into the dispensing probe 132 such that a liquid reagent micro droplet 150 with a predetermined volume is formed at the tip 144 and adheres to or is otherwise associated with the tip 144.

The controller 106 may shut off the liquid pump 134. After a predetermined amount of time, e.g., 1, 2, 3, 4, or 5 milliseconds, sufficient to stabilize the micro droplet 150 at the tip 144, the controller 106 may provide a control signal to the valve 128 to pulse a volume of pressurized gas through the gas nozzle 114 so that the gas nozzle 114 collimates the stream of gas and ejects a laminar gas stream through the nozzle opening 120 and through the travel path 124. The predetermined amount of time depends upon the viscosity of the liquid, and the parameters of the dispensing probe 132 and/or the tip 144. The predetermined amount of time may be more than or less than the exemplary range set forth above. In some exemplary embodiments, the laminar gas stream travelling through the travel path 124 travels substantially parallel to the sidewall 142 and applies a downward force on the micro droplet 150 at the tip 144. The amount of force is sufficient to separate the micro droplet 150 from the tip 144 and to carry or inject the micro droplet 150 into the target opening 156 of the target vessel 110 by the laminar gas stream. The micro droplet 150 may stabilize in a substantially spherical shape as it travels through the travel path 124 prior to being injected into the target vessel 110, for example.

Once the micro droplet 150 enters the cryogenic coolant chamber 154 of the target vessel 110, the micro droplet 150 is substantially instantly frozen into a reagent microsphere 160 (FIG. 8). A plurality of liquid reagent micro droplets 150 may be frozen to form reagent microspheres 160 in this manner. Once the desired number of frozen reagent microspheres 160 is formed, the reagent microspheres 160 may be removed from the target vessel 110, freeze-dried, and implemented with testing devices, for example.

As will be appreciated by persons of ordinary skill in the art, the distance separating the tip 144 and the target vessel 110, and the distance separating the tip 144 and the nozzle opening 120 may be adjusted to optimize the formation of the micro droplet(s) 150 at the tip 144 and to optimize the size and shape of the frozen reagent microspheres 160, so that the frozen reagent microspheres 160 are substantially uniform in size and shape, while at the same time preventing the liquid reagent from freezing inside the dispenser probe 132. Further, the volume and/or the pressure of the pressurized gas supplied to the gas nozzle 114 may be likewise adjusted to optimize the separation of the micro droplets 150 from the tip 144 and the injection of the micro droplets 150 in the target opening 156 of the target vessel 110, for example.

Referring now to FIG. 6, in some exemplary embodiments, a liquid micro droplet dispenser 100*a* according to the inventive concepts disclosed herein may be implemented with multiple liquid deposition systems 101, to form a multiple probe (or multiple channel) dispenser (e.g., a 4-probe dispenser) for higher throughput, such as by having two or more liquid deposition systems 101 including two or more, pumps (also referred to herein as a liquid pump assembly) 134, valves (also referred to herein as a valve assembly) 128 and/or a plurality of dispensing probes 132*a-n*, as will be appreciated by a person of ordinary skill in the art, to scale up the number of micro droplets 150 produced in a given amount of time. The liquid micro droplet dispenser 100*a* may include a common controller 106 for controlling the pumps 134 and valves 128 as discussed above in a simultaneous manner with the pumps 134 and/or valves 128 slaved together (e.g., common control line), or independently using separate control lines. For example, the liquid micro droplet dispenser 100*a* can be used to scale up the lyophilized reagent microsphere production capacity. In this embodiment, each of the dispensing probes 132*a-n* or groups of the dispensing probes 132*a-n* can be operated simultaneously or independently. For example, the pumps 134 and valves 128 can be operated to provide different volumes of liquid per micro droplet 150, or different types of liquids can be dispensed simultaneously.

As will be appreciated by persons of ordinary skill in the art, micro droplet dispensers 100 or 100*a* according to the inventive concepts disclosed herein may be implemented with any desired number of dispensing probes 132 (or channels), such as a single dispensing probe 132, two or more dispensing probes 132*a*, or a plurality of dispensing probes 132. For example, each dispensing probe 132 may be connectable or connected to a separate liquid pump, such as the liquid pump 134, and may dispense the same liquid reagent droplets, or two or more dispensing probes 132 may be connectable or connected to two or more liquid pumps and/or may dispense two or more different reagent droplets into the same or different target vessels.

Referring now to FIG. 7, an exemplary method 170 of using a micro droplet dispenser 100 to manufacture frozen reagent microspheres 160 according to the inventive concepts disclosed herein is described.

In a step 172, the controller 106 may activate the liquid pump 134 so that a predetermined volume of liquid reagent is pumped into the dispenser probe 132 and so that at least one micro droplet 150 is formed at the tip 144.

In a step 174, the controller 106 may deactivate the liquid pump 134. It is to be understood that in some exemplary embodiments, rather than deactivating the liquid pump 134, the controller may cause the liquid pump 134 to operate at a lower speed, for example.

In a step 176, the controller may wait the predetermined period of time after deactivating the liquid pump 134 as discussed above, so that the micro droplet 150 may stabilize at the tip 144.

In a step 178, the controller 106 may open the valve 128 for a predetermined amount of time, so that a pulse of pressurized gas is supplied to the gas nozzle 114 and ejected from the nozzle opening 120 as a laminar gas stream. The laminar gas stream may eject, blow-off, dislodge, or otherwise cause the micro droplet 150 to separate from the tip 144. The pulse of pressurized gas may be supplied for 1, 2, 3, 4, 5, or 6 milliseconds, and may be adjusted so as to release the micro droplet 150 from the tip 144. The laminar gas stream may guide or inject the separated micro droplet 150 into the target opening 156 of the target vessel 110, for example.

After the micro droplet 150 is injected into the target vessel 110, the controller may repeat steps 172 through 178 one or more times, so that a desired number of micro droplets 150 are injected into the target vessel 110 and a desired number of frozen reagent microspheres 160 are formed in the target vessel 110. The frozen reagent microspheres 160 may be removed from the target vessel 110 as desired, and may be freeze-dried and/or further processed for example.

It is to be understood that the steps disclosed herein may be performed simultaneously or in any desired order, and may be carried out by a human, or by a machine, and combinations thereof, for example. For example, one or more of the steps disclosed herein may be omitted, one or more steps may be further divided in one or more sub-steps, and two or more steps or sub-steps may be combined in a single step, for example. Further, in some exemplary embodiments, one or more steps may be repeated one or more times, whether such repetition is carried out sequentially or interspersed by other steps or sub-steps. Additionally, one or more other steps or sub-steps may be carried out before, after, or between the steps disclosed herein, for example.

As will be appreciated by persons of ordinary skill in the art, the application of micro droplet dispensers according to the inventive concepts disclosed herein may extend into any field that involves liquid handling. For example, non-contact liquid micro droplet dispensers according to the inventive concepts disclosed herein may be used to precisely deliver reagents and/or samples into wells on micro-titer plates. As will be appreciated, the dispenser probes of non-contact liquid micro droplet dispensers according to the inventive concepts disclosed herein typically would not be washed before depositing the same reagent or sample into multiple wells, because the non-contact dispensing avoids contamination of the dispenser probes.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed herein and as defined in the appended claims.

What is claimed is:

1. A non-contact micro-droplet dispenser, comprising:
a support;
a valve;
a controller operably coupled with the valve;
a gas injection assembly supported by the support, including a gas manifold having a gas nozzle and a nozzle opening configured to eject a substantially laminar gas stream so that the substantially laminar gas stream travels through a travel path;
a pressurized gas supply line fluidly connected with the gas nozzle and controlled by the valve;
a liquid delivery assembly including a dispensing probe having a sidewall including a first end having a liquid port and a second end having a tip, and a flow path opening at the tip and fluidly connected with the liquid port, the tip within the travel path;
a liquid pump operably coupled with the controller and fluidly connected to the liquid port of the dispensing probe, the liquid pump configured to deliver a volume of liquid to the dispensing probe so that at least one micro droplet is formed at the tip;
wherein the sidewall of the dispensing probe extends within the gas nozzle, and through the nozzle opening, a portion of the sidewall of the dispensing probe extending beyond the gas nozzle such that the flow path opening at the tip of the sidewall is located outside of the gas nozzle and in the travel path; and
wherein the laminar gas stream is configured to exert downward force on the micro droplet associated with the tip so that the micro droplet separates from the tip and is carried through the travel path by the laminar gas stream;
a target vessel positioned at a distance below the tip and having a target opening positioned so as to intersect the travel path, and wherein the substantially laminar gas stream is configured to inject the micro droplet into the target opening;
a temperature control system regulating a temperature within the target vessel to a predetermined temperature, characterized in that the temperature control system has temperature sensors, wherein the temperature sensors are positioned so as to detect at least one of the temperature inside the target vessel, at the target opening, or just above the target opening, and combinations thereof.

2. The non-contact micro-droplet dispenser of claim 1, wherein the gas nozzle is substantially cylindrical, and wherein the dispensing probe extends through the gas nozzle substantially coaxially with the gas nozzle.

3. The non-contact micro-droplet dispenser of claim 1, wherein the tip is positioned in the travel path such that the substantially laminar gas stream travels substantially parallel to the sidewall.

4. The non-contact micro-droplet dispenser of claim 1, wherein the target vessel is a cryogenically cooled target vessel.

5. The non-contact micro-droplet dispenser of claim 1, wherein the support movably supports the manifold such that the distance between the tip and the target opening is adjustable.

6. A non-contact micro-droplet dispenser, comprising:
a support;
a valve;
a gas injection assembly supported by the support, including:
a gas manifold having a gas nozzle and a nozzle opening configured to eject a substantially laminar gas stream so that the substantially laminar gas stream travels through a travel path;
a pressurized gas supply line fluidly connected with the gas nozzle and controlled by the valve;
a liquid delivery assembly including:
a liquid manifold supported by the support;
a dispensing probe having a tip positioned in the travel path;
a controller operably coupled with the valve;
a liquid pump operably coupled with the controller and fluidly connected with the dispensing probe, upon receiving a first signal from the controller, the liquid pump configured to deliver a volume of liquid to the dispensing probe so that at least one micro droplet is formed at the tip; and
wherein the controller opens and closes the valve to cause a substantially laminar gas stream to be ejected through the nozzle opening and thereby exert downward force on the micro droplet associated with the tip so that the micro droplet separates from the tip and is carried through the travel path by the substantially laminar gas stream;
a cryogenically cooled target vessel having a target opening positioned at a distance below the tip so as to intersect the travel path;
the distance between the tip and the target opening being adjusted so that the liquid in the dispensing probe and/or the micro droplet formed at the tip does not freeze.

7. The non-contact micro-droplet dispenser of claim 6, wherein the dispensing probe extending through the gas nozzle so that the tip extends a distance past the nozzle opening such that the tip is positioned in the travel path.

8. The non-contact micro-droplet dispenser of claim 6, further comprising a temperature control system includes one or more heat exchanger associated with the cryogenically cooled target vessel, one or more temperature sensors to determine the temperature within the cryogenically cooled target vessel, and a temperature controller to regulate the one or more heat exchanger based upon input from the one or more temperature sensors thereby regulating a temperature within the cryogenically cooled target vessel to a predetermined temperature.

9. The non-contact micro-droplet dispenser of claim 8, wherein the temperature control system regulates the temperature within the cryogenically cooled target vessel to below room temperature.

10. The non-contact micro-droplet dispenser of claim 8, wherein the cryogenically cooled target vessel is selected from a group consisting of a test tube, a vial, a cartridge, a well of a micro titer plate, and a microfluidic device.

11. The non-contact micro-droplet dispenser of claim 8, wherein the distance between the tip and the cryogenically cooled target vessel is adjustable.

12. The non-contact micro-droplet dispenser of claim 8, wherein the temperature control system has at least one temperature sensor just above the target opening.

13. The non-contact micro-droplet dispenser of claim 8, wherein the temperature control system has at least one temperature sensor outside of the cryogenically cooled target vessel.

14. A non-contact micro-droplet dispenser, comprising:
a plurality of liquid deposition systems, at least two of the liquid deposition systems comprising:
a liquid pump assembly;
a valve assembly;
a liquid delivery assembly including one or more dispensing probes having a sidewall including a first end having a liquid port and a second end having a tip, and a flow path opening at the tip and fluidly connected with the liquid pump;
a gas injection assembly including one or more manifolds having a gas nozzle, a nozzle opening, and a gas port connected to the valve, the gas nozzle configured to eject a substantially laminar gas stream through the nozzle opening so that the substantially laminar gas stream travels through a travel path, the one or more manifold positioned so that the tip of the one or more dispensing probe extends at least partially into the travel path; and
a controller controlling the liquid pump assemblies and the valve assemblies of the at least two liquid deposition systems to enable the liquid pump to cause at least one micro droplet to be formed at the tip when a volume of liquid flows through the flow path, and control the valve to enable a pulse of the laminar gas stream to separate the at least one micro droplet from the tip and carry the at least one micro droplet through the travel path, the controller being configured to independently control the liquid pump and the valve of one of the at least two liquid deposition systems relative to the liquid pump and the valve of another one of the at least two liquid deposition systems.

* * * * *